(12) United States Patent
Kochanek et al.

(10) Patent No.: US 8,628,512 B2
(45) Date of Patent: Jan. 14, 2014

(54) EMERGENCY PRESERVATION AND RESUSCITATION METHODS

(75) Inventors: Patrick M Kochanek, Pittsburgh, PA (US); Xianren Wu, Pittsburgh, PA (US); Samuel Aaron Tisherman, Pittsburgh, PA (US); S. William Stezoski, Pittsburgh, PA (US); Lyn Yaffe, Woodfield, MD (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 341 days.

(21) Appl. No.: 12/900,917

(22) Filed: Oct. 8, 2010

(65) Prior Publication Data

US 2011/0028961 A1 Feb. 3, 2011

Related U.S. Application Data

(62) Division of application No. 11/471,762, filed on Jun. 21, 2006, now abandoned.

(60) Provisional application No. 60/692,722, filed on Jun. 22, 2005.

(51) Int. Cl.
*A61M 31/00* (2006.01)
*A61F 7/12* (2006.01)

(52) U.S. Cl.
USPC ........................................ 604/507; 604/113

(58) Field of Classification Search
USPC ............................ 604/24, 500, 506, 507, 113
See application file for complete search history.

(56) References Cited

U.S. PATENT DOCUMENTS

| | | | |
|---|---|---|---|
| 3,374,066 A | 3/1968 | Farrant | |
| 3,425,419 A | 2/1969 | Dato | |
| 4,451,251 A | 5/1984 | Osterholm | |
| 5,149,321 A | 9/1992 | Klatz et al. | |
| 5,395,314 A * | 3/1995 | Klatz et al. | 604/24 |
| 5,407,428 A | 4/1995 | Segall et al. | |
| 5,584,804 A * | 12/1996 | Klatz et al. | 604/24 |
| 5,653,685 A | 8/1997 | Klatz et al. | |
| 5,709,654 A * | 1/1998 | Klatz et al. | 604/24 |
| 5,752,929 A * | 5/1998 | Klatz et al. | 604/506 |
| 5,755,756 A | 5/1998 | Freedman, Jr. et al. | |
| 5,827,222 A | 10/1998 | Klatz et al. | |
| 5,906,588 A | 5/1999 | Safar et al. | |
| 6,042,559 A | 3/2000 | Dobak, III | |
| 6,117,105 A | 9/2000 | Bresnaham et al. | |
| 6,149,624 A | 11/2000 | McShane | |

(Continued)

OTHER PUBLICATIONS

U.S. Appl. No. 11/471,762, Office Action dated Jul. 8, 2010.

(Continued)

*Primary Examiner* — Victoria P Shumate
(74) *Attorney, Agent, or Firm* — The Webb Law Firm

(57) ABSTRACT

Provided are methods for inducing preservation in a patient and resuscitating that patient. At least three hours of preservation, with successful resuscitation, are realized using the methods described herein. The methods involve flushing a patient with an oxygenated, cold-flush solution, such as normal saline, having an energy source. The patient may be cooled to deep or profound hypothermia to induce preservation. The patient may be resuscitated by warming to from about 33° C. to about 36° C., and then may be slowly warmed over a 24 to 72 hour period to normothermia. Kits for inducing preservation also are provided.

48 Claims, 5 Drawing Sheets

(56) References Cited

U.S. PATENT DOCUMENTS

| | | | |
|---|---|---|---|
| 6,149,670 A | | 11/2000 | Worthen et al. |
| 6,156,007 A | * | 12/2000 | Ash .............................. 604/113 |
| 6,336,910 B1 | | 1/2002 | Ohta et al. |
| 6,368,304 B1 | | 4/2002 | Aliberto et al. |
| 6,393,320 B2 | | 5/2002 | Laserolm et al. |
| 6,458,758 B1 | * | 10/2002 | Hsia ............................... 514/1.1 |
| 6,475,186 B1 | | 11/2002 | Safar et al. |
| 6,478,812 B2 | * | 11/2002 | Dobak et al. .................. 607/105 |
| 6,482,171 B1 | | 11/2002 | Corvi et al. |
| 6,485,450 B1 | | 11/2002 | Owen |
| 6,589,223 B1 | * | 7/2003 | Segall et al. ................... 604/500 |
| 6,692,519 B1 | * | 2/2004 | Hayes, Jr. ...................... 607/105 |
| 6,702,842 B2 | * | 3/2004 | Dobak et al. ................... 607/105 |
| 6,755,850 B2 | * | 6/2004 | Dobak, III ..................... 607/105 |
| 6,818,011 B2 | | 11/2004 | Dobak, III |
| 6,905,509 B2 | * | 6/2005 | Dobak et al. .................... 607/96 |
| 2003/0113278 A1 | * | 6/2003 | Hsia et al. ......................... 424/59 |
| 2003/0216688 A1 | | 11/2003 | M.A.J.M. et al. |
| 2004/0058432 A1 | | 3/2004 | Owen et al. |
| 2004/0158191 A1 | | 8/2004 | Samson et al. |
| 2005/0130906 A1 | | 6/2005 | Matier et al. |
| 2007/0123567 A1 | * | 5/2007 | Maxwell ......................... 514/327 |
| 2010/0121273 A1 | | 5/2010 | Kochanek et al. |

OTHER PUBLICATIONS

U.S. Appl. No. 11/471,762, Office Action dated Apr. 14, 2010.

Tisherman SA, et al.: Therapeutic deep hypothermic circulatory arrest in dogs: A resuscitation modality for hemorrhagic shock with 'irreparable' injury. J Trauma 30:836-847, 1990.

Bellamy R, et al.: Suspended animation for delayed resuscitation. Crit Care Med 24/S:S24-47, 1996.

Behringer W, et al.: Rapid hypothermic aortic flush can achieve survival without brain damage after 30 minutes cardiac arrest in dogs. Anesthesiology 93:1491-1499,2000.

Tisherman SA, et al.: Profound hypothermia <<1 OaC) compared with deep hypothermia (15aC) improves neurologic outcome in dogs after two hours' circulatory arrest induced to enable resuscitative surgery. J Trauma 31:1051-1062,1991.

Safar P, et al.: Suspended animation for delayed resuscitation from prolonged cardiac arrest that is unresuscitable by standard cardiopulmonary-cerebral resuscitation. Crit Care Med 28 (Suppl):N214-N218, 2000.

Nozari et al. Suspended animation and plasma exchange (SAPEX) enables full neorologic recovery from lethal traumatic exsandguination even after 2H Period of no-flow. Crit Care Med 31/12: A9 (2003).

Behringer W, et al.: Survival without brain damage after clinical death of 60-120 min in dogs using suspended animation by profound hypothermia. Crit Care Med 31:1523-1531, 2003.

Behringer W, et al.: Antioxidant Tempol enhances hypothermic cerebral preservation during prolonged cardiac arrest in dogs. J Cereb Blood Flow Metab 22:105-117, 2002.

Tisherman S: Suspended animation for resuscitation from exsanguining hemorrhage. Proceedings from the Safar Symposium, Oct. 2003. Crit Care Med. Feb. 2004:32(2 Suppl):S46-50.

Behringer et al. Crit Care Med 27/12:A65 (1999).

Chadha et al. Crit Care Med 30/12:A24 (2002).

Dexter F, et al.: The brain uses mostly dissolved oxygen during profoundly hypothermic cardiopulmonary bypass. Ann Thorac Surg. Jun. 1997;63(6):1725-9.

Robbins RC, et al.: Intermittent hypothermic asanguineous cerebral perfusion (cerebroplegia) protects the brain during prolonged circulatory arrest. A phosphorus 31 nuclear magnetic resonance study. J Thorac Cardiovasc Surg 99:878-84, 1990.

Sato Y, et al.: Differential cerebral gene expression during cardiopulmonary bypass in the rat: evidence for apoptosis? Anesth Analg 94:1389-94, 2002.

Jenkins LW, et al.: Conventional and functional proteomics using large format two-dimensional gel electrophoresis 24 hours after controlled cortical impact in postnatal day 17 rats. J Neurotrauma 19:715-740, 2002.

Aksenov MY, et al.: Protein oxidation in the brain in Alzheimers disease. Neuroscience 103:373-383, 2001.

Clark RS, et al.: Caspase-3 mediated neuronal death after traumatic brain injury in rats. J Neurochem 74:740-753, 2000.

Clark RS, et al.: Increases in Bcl-2 and cleavage of caspase-1 and caspase-3 in human brain after head injury. FASEB J 13:813-821: 1999.

Zhang X, et al.: Intranuclear localization of apoptosis-inducing factor (AIF) and large scale DNA fragmentation after traumatic brain injury in rats and in neuronal cultures exposed to peroxynitrite. J Neurochem 82:181-191,2002.

Petrosillo G, et al.: Role of reactive oxygen species and cardiolipin in the release of cytochrome c from mitochondria. FASEB J 17:2202-2208,2003.

Bazan, Biochim Biophys Acta 218:1-10 (1970).

\* cited by examiner

EMERGENCY PRESERVATION AND RESUSCITATION METHODS

CROSS REFERENCE TO RELATED APPLICATIONS

This application is a divisional application of U.S. patent application Ser. No. 11/471,762, filed Jun. 21, 2006 now abandoned, which claims the benefit under 35 U.S.C. §119(e) to U.S. Provisional Patent Application No. 60/692,722, filed Jun. 22, 2005, each of which is incorporated herein by reference in its entirety.

STATEMENT REGARDING FEDERALLY SPONSORED RESEARCH AND DEVELOPMENT

This invention was made with government support under Telemedicine and Advanced Technologies Research Center Grant No. DAMD17-01-02-0038 awarded by the US Army Medical Research and Materiel Command. The government has certain rights in this invention.

BACKGROUND

1. Field of the Invention

Emergency preservation and resuscitation methods are provided, along with kits for implementing those methods in the field.

2. Description of the Related Art

Emergency preservation and resuscitation is, without limitation, the therapeutic induction of a state of tolerance to temporary, complete systemic ischemia (deficiency of blood supply). Emergency preservation and resuscitation is an interventional preservation measure for patients/victims who cannot be immediately resuscitated, for example and without limitation, in pre-hospital, hospital and field scenarios. These patients may be prevented from dying by inducing such preservative measures until evacuated to a medical center for emergency medical/surgical intervention and delayed resuscitation can be completed. These victims would otherwise die at the point-of-injury or in the field because definitive medical/surgical procedures are not immediately available and/or could not be brought to the point-of-injury. The potential emergency medical market sector for use is very large. Approximately 1,200-1,500 victims each day in the United States alone die from sudden cardiac arrest that cannot be reversed or recovered in the field through defibrillation or other currently available advanced cardiopulmonary cerebral resuscitation techniques. Trauma victim deaths add another 250 cases per day in the United States that may benefit from life-saving emergency preservation and resuscitation procedures. This number due to trauma could be substantially greater during warfare or terrorist attack. These trauma and sudden cardiac arrest victims could potentially be protected by deep, profound or ultra-profound hypothermia, as may be necessary, enabling evacuation to a medical center followed by more sophisticated, hospital-based, life-saving interventions. However, current methods for reproducibly preserving life during a cardiopulmonary arrest of more than one-to-two hours in duration are not available.

U.S. Pat. No. 5,149,321 to Klatz et al. (the '321 patent) discloses a method and devices purportedly useful in resuscitating the brain of a patient suffering from ischemic and anoxic injury using oxygenated fluids. The fluids are introduced into one or both of the external carotid arteries. The fluid is oxygenated and contains: barbiturates; oxygen carrying agents; antioxidants; Lazeroids; carrier vehicles, preferably dimethyl sulfoxide (DMSO) and, optionally, physiological buffers; nutrients, such as glucose; and "other chemicals," such as an anticoagulant). The fluid is delivered at approximately 40° F. (4.44° C.). An integrated device, including a reservoir, oxygenator, pump and logic control unit, useful in delivering the fluid to a patient is disclosed in the '321 patent. The '321 patent does not disclose or suggest use of saline-based aqueous solutions, does not address the need to reach any target brain (tympanic) temperature, does not disclose whole-body flushing, does not provide any details on how to resuscitate the patient, and, importantly, does not indicate that they can achieve successful resuscitation using those methods.

U.S. Pat. No. 5,827,222 to Klatz et al. is a member of a chain of Continuations-In-Part of a Divisional of the '321 patent. It further describes organ preservation techniques that involve flushing a patient's circulatory system and/or body cavities with a chilled organ preservation solution. The organ preservation solution, as with the brain preservation solution described in the '321 patent, is preferably a DMSO-based solution, with no disclosure of the usefulness of a saline-based solution. This reference does not disclose or suggest use of saline-based aqueous solutions, does not address the need to reach any target brain (tympanic) temperature, does not provide any details on how to resuscitate the patient, and, importantly, does not indicate that they can achieve successful resuscitation using those methods.

U.S. Pat. No. 6,485,450 to Owen discloses an integrated device useful in delivering fluids, as in the methods described in the '321 patent. The fluid is described as a "medical fluid," which may be blood or crystalloid solution. As above, no resuscitation techniques are mentioned and no success in resuscitation is discussed.

In Behringer et al. (Behringer W, Safar P, Wu X, Kentner R, Radovsky A, Kochanek P M, Dixon C E, Tisherman S A, "Survival without brain damage after clinical death of 60-120 min in dogs using suspended animation by profound hypothermia," *Crit Care Med* 31:1523-1531, 2003), dogs that were exsanguinated to cardiac arrest recovered fully, with normal functionality when flushed with normal saline at 2° C. to a tympanic temperature of 10° C. The dogs were resuscitated by closed-chest cardiopulmonary bypass, postcardiac arrest mild hypothermia (tympanic temperature 34° C.) to 12 hrs, controlled ventilation to 20 hrs, and intensive care to 72 hrs. Notably, two of the four dogs treated in this manner suffered moderate-to-severe overall disability ratings with less-than-normal neurological deficit scores.

Although reaching the two-hour mark for normal resuscitation is significant, it is not quite a workable time frame for many field injuries, especially battlefield injuries, which require transport by helicopter or other means, often from remote locations. This transport time, when added to the time required for patient evaluation and intervention, which can be complex in many trauma cases, uses up the two-hour resuscitation window quite rapidly. Therefore, a three or more-hour window is very much desired. In addition, an approach with more reliable intact neurological outcome for durations of less than three hours is also desirable.

SUMMARY

Induction of an emergency preservation and resuscitation method is desirable in many cases, including, without limitation: (1) severe trauma followed either by rapid exsanguination (massive bleeding) or slow bleeding and prolonged hemorrhagic shock, and, in either case cardiopulmonary arrest; (2) unresuscitable cardiac arrest unresponsive to defibrillation; (3) severe stroke; (4) specific in-hospital scenarios including cardiac arrest and cardiac surgeries; and (5) other life-threatening medical emergencies, including toxin, venom and poisoning exposures, chemical and biological warfare agents, drug overdoses, drowning, decompression sickness, asphyxiation and respiratory arrest, and other deaths due to potentially reversible conditions. After inducing emergency, the immediate cause of death can be eliminated/reversed within three hours.

A method of inducing emergency preservation for at least about three hours in a patient suffering from cardiopulmonary arrest is provided. The method comprises cooling the patient within about 8 minutes of cardiopulmonary arrest or cessation of cardiopulmonary resuscitation by flushing patient's vasculature, with an oxygenated cold-flush solution comprising an energy source, wherein the cold-flush solution is introduced into the patient at from about 1° C. to about 4° C. and the patient is cooled to a tympanic temperature of less than about 20° C. in a time period of less than about 30 minutes. The cold-flush solution is aqueous, for example normal saline, and may be isotonic or mildly hypertonic. The patient preferably is cooled to a target tympanic temperature of less than 10° C. and typically to about 7° C. The patient preferably is cooled to the target tympanic temperature within 20 minutes.

The patient is resuscitated by warming combined with re-introduction of blood, typically using a heart-lung bypass machine. The patient preferably is warmed within about three hours of initiation of emergency preservation by introducing blood into the patient's vasculature and warming the patient to a state of mild hypothermia at from about 33° C. to about 36° C. At that point, the method comprises raising the patient's temperature from mild hypothermia to about 37° C. over a time period of from about 24 to about 72 hours, typically 48 to 72 hours.

The cold-flush solution typically is introduced into the patient through the patient's arteries, for example through the patient's aorta. The patient may be decompressed by cannulation of the jugular vein, right atrium or vena cava.

The cold-flush solution further may comprise one or more nitroxide antioxidants, such as TEMPO or TEMPOL, oxygen carriers, such as polynitroxylated albumin and polynitroxylated hemoglobin, or drugs. In one embodiment, the cold-flush solution is normal saline supplemented with from about 0.1% to about 5% dextrose, and in one example, 2.5% dextrose.

In another embodiment, a method of resuscitating a patient from emergency preservation is provided in which the patient has been subjected to induction of emergency preservation by flushing the patient's brain or vasculature with a cold-flush solution to induce hypothermia. The method comprises: (a) introducing blood into the patient's vasculature and warming the patient to a state of mild hypothermia at from about 33° C. to about 36° C., typically by cardiopulmonary bypass; and further warming the patient to about 37° C. over from about 24 hours to about 48 hours.

Also provided is a method of preserving organ function for transplant in a cadaver, comprising, cooling the cadaver by flushing the cadaver's blood vessels with an oxygenated cold-flush solution comprising an energy source, wherein the cooling solution is about 1° C. to about 4° C. and the cadaver is cooled to a tympanic temperature of less than about 10° C. in a time period of less than about 30 minutes.

For implementing the methods described herein, a kit is provided. The kit may be used in any setting, for example and without limitation, either in the field or in a hospital or trauma bay setting. In one embodiment, the kit comprises: (a) an access cannulation set, typically an arterial or aortic cannulation set; (b) a cold-flush solution reservoir typically containing an aqueous, cold-flush solution comprising an energy source; and (c) a pump configured to deliver the cold-flush solution through the arterial cannulation set and into a patient. The cold-flush solution either is oxygenated or the kit comprises an oxygenator configured to oxygenate the cold-flush solution prior to delivery of the cold-flush solution to a patient.

In one embodiment, the reservoir is insulated and the aqueous cold-flush solution is between 0° C. and about 4° C. In other embodiments, the kit may contain various combinations of items, including, without limitation an indicia describing a procedure for use of the kit in inducing emergency preservation, a tympanic thermometer, a decompression cannula, a pump, a heat exchanger, a computerized control and/or an oxygenator. The pump, heat-exchanger, cold-flush solution reservoir, computerized control and pump may be integrated. In certain embodiments, the kit further comprises one or more of a cold-flush solution temperature sensor, a pump flow rate sensor, a tympanic temperature sensor and a cold-flush solution oxygen sensor.

In yet another embodiment, a method of protecting organs of a cadaver is provided. The method comprises cooling the cadaver with a cold-flush solution, for example normal saline, wherein the cooling solution is about 1° C. to about 4° C. and the cadaver is cooled to a tympanic temperature of less than about 10° C. in a time period of less than about 20 minutes. Likewise, a method of transplanting organs of a cadaver, wherein the organs of the cadaver are protected by a method described above, the method comprising removing an organ of the cadaver for transplantation (harvesting the organ), and optionally re-introducing blood into the cadaver and warming the cadaver prior to harvesting the organ.

In another embodiment, a cold-flush solution is provided, as described above, comprising an oxygenated, aqueous solution comprising an energy source. The cold-flush solution may be isotonic or mildly hypertonic. The cold-flush solution may be between 0° and about 2° C. and may be saturated with oxygen. In use, the cold-flush solution may be contained within one of an arterial cannula and an aortic cannula. The cold-flush solution may comprise one or more of an antioxidant, and oxygen carrier, a drug, a perfluorocarbon, a glucose analog and an energy substrate.

DETAILED DESCRIPTION

Figure 1:
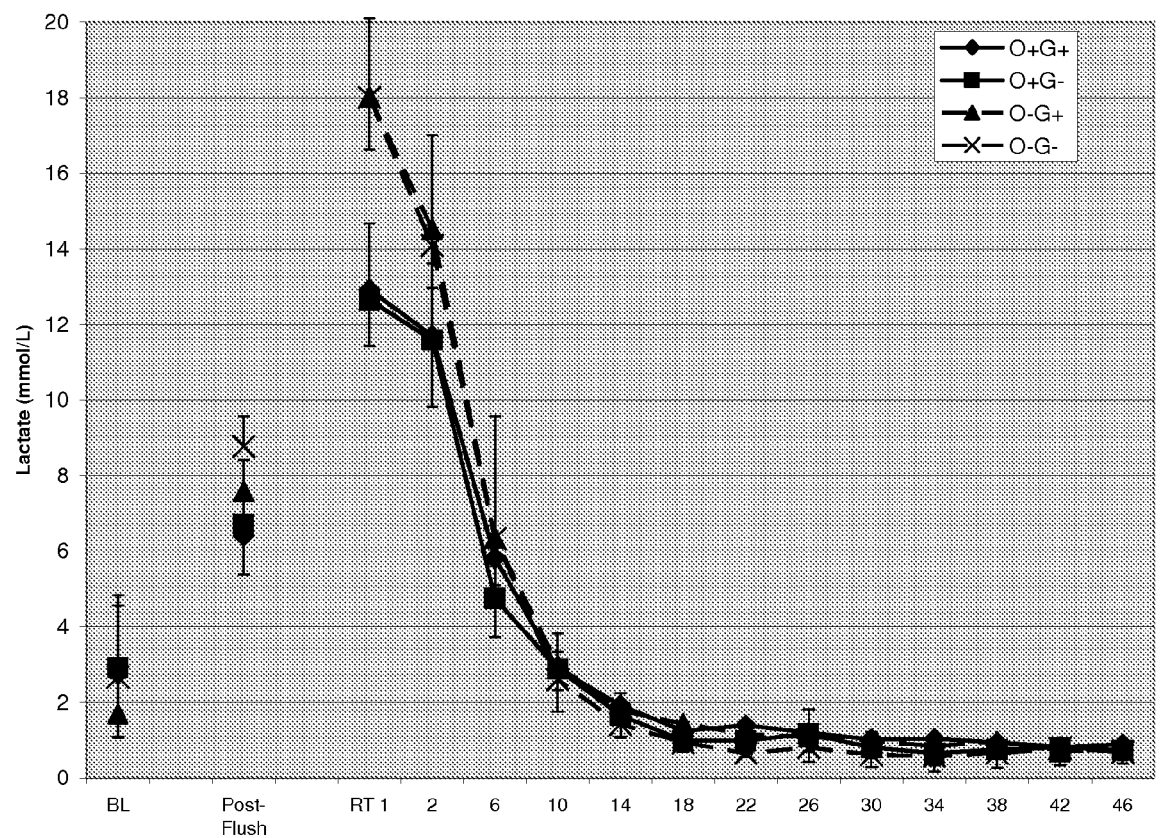
FIG. 1 is a graph showing arterial lactate level during emergency preservation of dogs for 3 h cardiac arrest.

The use of numerical values in the various ranges specified in this application, unless expressly indicated otherwise, are stated as approximations as though the minimum and maximum values within the stated ranges were both preceded by the word "about." In this manner, slight variations above and below the stated ranges can be used to achieve substantially the same results as values within the ranges. Also, the disclosure of these ranges is intended as a continuous range including every value between the minimum and maximum values.

Methods are provided for inducing emergency preservation (as used herein, "emergency preservation is synonymous with "suspended animation"), along with kits for inducing emergency preservation in the field. In its broadest sense, the method involves flushing a patient's or cadaver's vasculature with cold-flush solution, for example and without limitation, cold, oxygenated saline containing an energy source. The cold-flush solution is administered typically at greater than 0° C. to about 4° C. to a target tympanic temperature of between about 4° C. to about 20° C. Higher temperatures might be considered for shorter durations than 3 hours of emergency preservation. As used herein, "deep hypothermia" refers to a tympanic temperature of from about 11° C. to about 20° C., "profound hypothermia" refers to a tympanic temperature of from about 6° C. to about 10° C. and "ultra-profound hypothermia" refers to a tympanic temperature of less than or equal to about 5° C. The examples provided herein use profound hypothermia, with a typical tympanic temperature of about 7° C., but the target tympanic temperature may be selected in light of the duration of emergency preservation desired or by the amount of cold flush solution available. For example, a target tympanic temperature of 15° C. may be selected, but only may yield an emergency preservation time frame of 90 minutes using the oxygenated, energy-containing cold-flush solutions described herein.

The cold-flush process typically is initiated within 4-8 minutes of cardiopulmonary arrest, preferably within two minutes of cardiopulmonary arrest, or cessation of resuscitation attempts (such as, without limitation CPR) and is administered over less than about 30 minutes and preferably less than about 20 minutes. When emergency preservation is initiated in this manner, it is expected, based on the animal studies described herein, that a patient may be resuscitated three hours later, or even later, and may regain substantial, if not normal neurological function. During emergency preservation, medical personnel have a substantial window in which they can repair or otherwise counteract the cause of death. A patient is then resuscitated, typically by cardiopulmonary bypass, by raising his/her body temperature to a point at which a spontaneous heartbeat, and optimal cardiovascular hemodynamics are achieved, typically from about 33° C. to about 36° C., and the patient is removed from bypass, and the patient's temperature is then raised slowly over a period of from about 24 to about 72 hours to normal temperature (37° C.).

Induction of emergency preservation is desirable in many cases, including, without limitation: (1) severe trauma followed either by rapid exsanguination (massive bleeding) or slow bleeding and prolonged hemorrhagic shock, and, in either case cardiopulmonary arrest (2) unresuscitable cardiac arrest unresponsive to defibrillation; (3) severe stroke; (4) specific in-hospital scenarios including cardiac arrest and cardiac surgeries; and (5) other life-threatening medical emergencies, including toxin, venom and poisoning exposures, chemical and biological warfare agents, drug overdoses, drowning, decompression sickness, asphyxiation and respiratory arrest, and other deaths due to potentially reversible conditions. As used herein, the phrase "poisoning event(s)" means contact of the patient with a potentially lethal agent, chemical, compound or any composition of matter, including, but not limited to: a toxin; a chemical or biological warfare agent; a poison; a venom; a chemical compound; or a drug, as in the case of an overdose or lethal reaction.

For example and without limitation, in the setting of exsanguination, where uncontrolled internal bleeding leads to cardiopulmonary arrest, the victim might receive emergent aortic cannulation and jugular or right atrial cannulation. In one embodiment, a rapid intra-aortic flush of from about 1° C. to about 2° C. normal saline fully saturated with dissolved oxygen and including 2.5% dextrose is performed to achieve a target tympanic temperature of approximately 7° C. The flush typically is completed in less than 20 minutes and target temperature achieved. Flush volume may require as much as 500-600 ml/kg. Drainage of the flush solution occurs spontaneously from the jugular, atrial or vena caval cannula.

The cold-flush solution may be delivered either using a cardiopulmonary bypass device or a specially-designed apparatus for induction of emergency preservation. The cold-flush solution may also include oxygen carriers such as an artificial hemoglobin or hemoglobin substitute of all types and/or other energy substrates. Resuscitation may be performed after surgery, or even during surgery if necessary, using cardiopulmonary bypass. It is important to maintain the victim under mild hypothermia (preferably with full ICU care) for at least about 24 to about 72 hours with very slow re-warming. This entire procedure would be identical in the setting of normovolemic cardiopulmonary arrest with the exception that surgery would not be required to repair tissue trauma, but definitive therapy could include interventions such as initiation of cardiopulmonary bypass, an artificial heart, or administration of anti-toxin, anti-venom, or other appropriate antidote or therapy.

Limited medical technology is available for emergency preservation induction or similar therapy to save the lives of trauma victims with otherwise lethal injuries or patients with intractable cardiac arrest. The greatest advantages of the methods and kits described herein are: (1) their life-saving potential for patients/victims who would otherwise die from injuries and/or cardiac arrest; (2) the relative ease of emergency preservation induction through a well-planned and integrated emergency preservation kit (EP-Kit) providing all necessary components for performing emergency preservation induction with cold-flush solutions, additions and equipment; and (3) the lack of any viable competitive technologies or alternatives.

The methods described herein can be applied to a cadaver, having suffered lethal brain injury. Application of the methods described herein can preserve the internal organs of that cadaver for transplant purposes. In such a case, the cadaver may be transported after induction of emergency preservation. Alternately, the organs of a cadaver might be harvested after induction of emergency preservation, but before transport, before or after re-warming, as the case may be with a patient who does not survive the emergency preservation procedure. Optionally, prior to organ harvest, the cadaver may be treated with a cardiopulmonary bypass using a heart-lung machine (also known as a pump-oxygenator) to re-introduce blood, or provide cold perfusion, into the internal organs prior to harvesting/transplant. As resuscitation and recovery of proper brain and neurological function is not a concern in this situation, the window prior to re-introduction and re-warming can likely be extended well past three hours.

Emergency preservation may be induced by flushing a patient's vasculature through an artery with, for example and without limitation, cold, oxygenated saline with 2.5% dextrose (glucose). Patient (victim) flushing is accomplished by any suitable method for replacing the patient's blood volume with the cold-flush solution. By "flushing a patient's vasculature," it is meant that fluid is introduced into the patient's vasculature, with the goal of flushing a substantial portion of the patient's vasculature that remains intact and/or contiguous with the vasculature into which the fluid is introduced. It is most desirable to flush the brain and all major organs, though 100% flushing of a patient's vasculature is not practicable, if not impossible, especially in trauma patients.

In one non-limiting embodiment, the cold-flush solution is introduced into the aorta and the patient's blood, and eventually the cold-flush solution, is drained through the patient's jugular vein or right atrium (decompression). A person of skill in the medical arts and/or otherwise familiar with human vasculature will appreciate that there are many suitable arterial access points through which cold-flush solution may be introduced into the patient, including, without limitation, for aortal introduction: femoral, carotid, subclavian and brachial/axillary arteries, in which a catheter can be introduced to permit placement in the descending/thoracic aorta. Likewise, the jugular vein, right atrium and inferior or superior vena cava are suitable, but non-exclusive decompression points, which will be known to those of skill in the medical arts.

In one embodiment, the cold-flush solution is introduced into the aorta via a balloon catheter introduced into the aorta via a peripheral artery, such as the femoral, carotid, subclavian or brachial/axillary arteries. The patient is decompressed through the jugular vein, right atrium or vena cava. This method might not be preferred for use in the field without equipment that permits visualization of the catheter's positioning in the aorta (typically radiological equipment), but may be preferred as the least traumatic approach for hospitalized patients or patients in trauma bays or MASH (Mobile Army Surgical Hospital) units, or, possibly, like units (for example, MASH(-), Combat Support Hospitals, Forward Surgical Teams and Forward Surgical Elements, provided they are equipped with sufficient radiological capabilities or other visualization equipment).

In yet another embodiment, the cold-flush solution is introduced transthoracically. This may be accomplished through use of external thoracic landmarks and/or use of visualization methods and equipment. As such, this method is currently best suited for use in a hospital, trauma bay or MASH setting having appropriate radiological equipment. Direct access to the ascending aorta and aortic arch for the cold flush catheter is achieved via a transthoracic approach that permits the guided insertion of a cold flush catheter, for example, through the right chest wall, parasternally, directly into the ascending aorta with catheter advancement through the aortic arch and placement in the thoracic/descending aorta.

In a further embodiment, a thoracotomy is performed on the patient, permitting direct visualization of the aorta insertion point and the right ventricle drainage point. Although the most traumatic approach, it is an effective field technique for flushing the patient's system without using sophisticated visualization techniques, particularly in the case of battlefield injuries. Considering the alternative (death), this is a valid option, absent suitable guidance, devices and visualization equipment and methods permitting transthoracic or peripheral arterial introduction methods.

In certain patients with substantial trauma, interrupting contiguous blood flow among the brain, spinal column and abdominal organs, the cold-flush solution may be introduced by more than one route. In such situations, appropriate cannulation and shunts may be used to span the gap between major arteries/veins. The applicability of this technique must be determined on a case-by-case basis, as each patient typically suffers different injuries.

By the terms "suffer," "suffering" and "suffers" in reference to an injury, disease, condition, physiological state or event in or pertaining to a patient, it is meant that the injury, disease, condition, physiological state or event is objectively present in the patient and does not require that the person subjectively suffers in the sense that the patient experiences pain, agony, anxiety, fear or the like.

Irrespective of the method of flushing the patient, the goal is to reach a target brain temperature (as measured by its proxy, tympanic temperature) within as rapid a time as possible. Target tympanic temperatures are from about 4° C. to about 20° C., preferably profound hypothermic temperatures including, but not exclusively about 7° C. As such, the cold-flush solution is administered at as cold a temperature as possible while avoiding formation of ice crystals, especially at the point of introduction. Hence, the temperature of the solution is greater than 0° C. and less than about 4° C., preferably from about 1° C. to about 2° C. With adequate flow rates, cooling the patient to the target temperature within about 30 minutes, and preferably less than 27 minutes, and typically within about 15 to about 20 minutes. It should be realized that the target temperature need not be 7° C., though the lower the target temperature, the longer the patient is expected to be able to remain under emergency preservation. Higher temperatures might be considered for shorter durations than 3 hours of emergency preservation. It should be recognized that emergency preservation should be initiated within 10 minutes, preferably within 8 minutes and most preferably within 2 minutes of cardiopulmonary arrest or cessation of cardiopulmonary resuscitation to prevent loss of brain function due to anoxia and/or lack of energy sources. At some point after cardiopulmonary arrest, the patient cannot recover from emergency preservation, so the earlier the process is initiated after cardiopulmonary arrest and/or removal from resuscitative influences, such as CPR, the better.

The examples provided below indicate that when emergency preservation is induced using an oxygenated, aqueous, isotonic cold-flush solution, for example and without limitation, an oxygen-saturated 2° C. normal saline solution containing 2.5% dextrose, and emergency preservation is induced within about 30 minutes to a target tympanic temperature of from about 4° C. to about 10° C., and, for example about 7° C., a patient likely can be resuscitated at any time within at least about three hours of reaching the target tympanic temperature. A patient is typically resuscitated by re-infusion of type-matched blood using, for example and without limitation, a common heart-lung bypass machine until the patient's temperature reaches the point at which stable, optimized cardiovascular hemodynamics are seen, typically from about 33° C. to about 36°, and often about 34° C. The patient is then slowly warmed to 37° C. over 24 to 72 hours, more typically from 48 to 72 hours.

The cold-flush solution typically is an oxygenated, aqueous solution containing a suitable energy source. In one embodiment, the solution is normal saline (from about 0.85% w/v to about 0.9% w/v NaCl), which is broadly available. Other examples of aqueous solutions believed to be useful in the induction of emergency preservation include, without limitation: Lactated Ringers, Plasmalyte, Normosol (Abbott), U-W solution (Viaspan), 5% albumin, Plasmanate (Bayer Healthcare), hydroxyethyl starch and dextran solutions or other known blood substitutes. By "isotonic," it is meant that the solution has substantially the same tonicity as some other solution with which it is compared, namely blood serum in the context of the present application. Mildly hypertonic solutions, such as hypertonic saline (1.0% w/v to about 1.5% w/v NaCl), may prove useful in the methods described herein. By "mildly hypertonic," it is meant a solution having the tonicity of from 0.9% w/v saline to about 1.5% w/v saline.

The cold-flush solution is oxygenated, and in one embodiment, to saturation. In practice, it should be recognized that complete or absolute 100% saturation is impossible to achieve and/or maintain due to microscopic or macroscopic temperature fluctuations and variations in methodology used to saturate the fluid and maintain the saturation, resulting in sub-saturation and super-saturation, often depending upon the temperature and composition of the fluid. For this reason the terms "saturate," "saturated" and "saturation" are approximates of 100% saturation, and, in practice, typically range ±10%, ±5%, ±2% or ±1%, or less, including increments therebetween. As used herein, the terms "saturate," "saturated" and "saturation" therefore include such variation in saturation levels as are normally experienced with fluids prepared, maintained and used in the manner described herein. Oxygen saturation of the cold-flush solution maybe achieved by any known method for introducing gasses into a liquid, for example and without limitation, by insufflation using a cardiopulmonary bypass machine. Although saturated oxygen may be preferred, sub-saturated oxygen levels also may prove useful. The terms "oxygenated" and "oxygenate" refer to artificially increased oxygen levels or increasing the oxygen levels in a solution, such as the cold-flush solution.

The cold-flush solution also contains an energy source. In one embodiment, the energy source is 2.5% w/v dextrose (D-glucose) in normal saline. The amount of dextrose in the cold-flush solution may deviate from about 2.5% w/v, with useful ranges of from about 0.5% to about 5%, from about 1% to about 4% and from about 2% to about 3%. Other potentially suitable energy sources include: lactate, beta-hydroxy butyrate, Ringers ethyl pyruvate solution, adenosine triphosphate (ATP) and inorganic phosphates. These other energy substrates may be used alone or in combination with dextrose/glucose Ingredients other than oxygen and an energy source may be added to the cold-flush solution. These ingredients include, without limitation: antioxidants, such as, for example nitroxide spin traps such as TEMPO (2,2,6,6-tetramethylpiperidine-1-oxyl) and TEMPOL (4-hydroxy-2,2,6,6-tetramethylpiperidine-N-oxyl); oxygen carriers, for example, polynitroxylated hemoglobin (SynZyme, Irvine, Calif.), polynitroxylated albumin (SynZyme, Irvine, Calif.), pyridoxalated polymerized hemoglobin solution (PolyHeme, commercially available from Northfield Laboratories, Inc. of Evanston, Ill.) and Hemopure® (hemoglobin glutamer-250), commercially available from Biopure Corporation, Cambridge, Mass. and perfluorocarbons, such as PHER-O2, commercially available from Sanguine Corporation of Pasadena, Calif. or Fluosol; and Perfulbron (Oxygent), Alliance Pharmaceuticals, San Diego, Calif. In the case of oxygen carriers, polynitroxylated hemoglobin derivatives may be preferred over free hemoglobin as free hemoglobin releases iron in vivo, with potential adverse effects.

A variety of neuroprotective agents could be added to cold-flush including, without limitation: traditional anesthetics such as barbiturates (thiopental, pentobarbital), ketamine, or opioids; anticonvulsants such as phenyloin or valproate; anti-apoptotic agents such as caspase inhibitors or kinase inhibitors such as mitogen-activated protein kinase inhibitors; and/or protease inhibitors such as calpain antagonists. Finally, anti-inflammatory agents such as, without limitation: a cyclosporin, such as cyclosporine-A, FK 506, methyl prednisolone, cyclooxygenase-2 antagonists, antagonists of pro-inflammatory cytokines such as TNF-alpha or Interleukin (IL)-1, or the anti-inflammatory cytokine IL-10 could be added to the flush solution to confer cerebral protection and/or protection against multiple organ failure.

Use of proper resuscitative methods is important to the recovery of patients who have undergone emergency preservation. Resuscitation may begin at any time after induction of emergency preservation. In one embodiment, definitive treatment of the underlying injury or event is completed prior to initiation of resuscitation. In another embodiment, for example in cases where treatment cannot be completed within the three hour emergency preservation window, resuscitation can be completed before the patient is completely treated. In such a case, prioritization of treatments is required to ensure that the patient does not die from the sustained injuries or events during resuscitation. For example, injuries to major organs and vasculature may be repaired while the patient is under emergency preservation, and injuries to peripheral limbs may be repaired while the patient is being resuscitated. Resuscitation typically is accomplished by re-infusion of blood by use of a heart-lung bypass machine, as are commonly used in surgical facilities. The patient can be warmed to mild hypothermia, typically from about 33° C. to about 36° C., often 34° C., at which point the patient develops stable, optimized cardiovascular hemodynamics and potentially can be removed from the heart-lung bypass machine. The patient is then slowly warmed to 37° C. over about a 24 to 72 hour period, preferably over from about 48 to about 72 hours. The patient typically is kept under Intensive Care supervision during that time period.

Although specialized equipment may be designed for induction of emergency preservation by the methods described herein, much of the equipment used to induce emergency preservation can be stock or common equipment, ranging from trocars and catheters to heart-lung bypass machines. Further many of the steps can be accomplished using a variety of different methods. As such, the steps of flushing a patient with cold-flush solution and resuscitating the patient are central, while the nature of the implementing devices may vary greatly. Required devices include an access cannulation set, which is a device or set of devices for introducing the cold-flush solution into the patient, for example and without limitation, through the thoracic aorta or femoral artery. The access cannulation set typically is an arterial or aortic cannulation set. A typical access cannulation set might include a trocar, an inserter or guide, and a sealing or occluding catheter, such as a balloon catheter of sufficient size to occlude the aorta. Although suitable cannulae or catheters are very common, non-limiting example of an arterial catheter are the Endoclamp-ST aortic catheter, available from Cardiovations, Ethicon, Inc. of Somerville, N.J. and catheters described in U.S. Pat. No. 6,482,171.

Although not literally required, a decompression cannulation set also may be used. This decompression cannulation set may simply be a large gauge needle for insertion into the patient's jugular vein or right atrium, or a trocar/inserter/cannula (or catheter) combination. The decompression cannulation set is a set of equipment that is used to facilitate drainage of blood and cold-flush solution from the patient. The decompression cannulation set may contain fluid adapters and tubing for connection to a pump and heat exchange for cooling, oxygenating and recirculating the cold-flush solution. Recirculation of the cold-flush solution may be desirable in certain instances, such as to preserve cold-flush solution.

Other access catheter features might include, temperature, flow and pressure sensors to assist in monitoring the status and course of emergency preservation. Each catheter may include a short length of coiled catheter tubing to provide extendibility of the catheter length during connection to the cold flush delivery system, as well as avoidance of catheter movement following arterial or aortic placement during patient transport. The cannulae or catheters are designed or selected to have the capability of delivering a large volume of cold-flush solution into the patient's vasculature, for example and without limitation, the patient's aorta or femoral artery, within 5-15 minutes, as may be necessary. Although systemic perfusion is preferred, immediate and targeted emergency hypothermia interventions might target vital organs such as the heart, brain, spinal cord and associated vasculatures (followed by global cold perfusion and hypothermia) and thereby impose a state of clinical preservation until transport can be provided to a facility for acute surgical care and delayed resuscitation. Catheters also may be suitably configured to permit their use as respective arterial and venous perfusion cannulae during cardiopulmonary bypass and delayed resuscitation, and potential use during re-warming, plasma exchange and mild-to-moderate hypothermic phases post-delayed resuscitation and transition to normovolemic spontaneous circulation.

As used herein, in reverence to transfer of fluids into and from vasculature a "cannula" refers to a tube for insertion into a blood vessel. During insertion of a cannula, its lumen is usually occupied by a trocar. In the same context, a "catheter" is a tubular, typically flexible, surgical instrument that is inserted into a blood vessel to withdraw or introduce fluid. As used herein, a catheter is considered to be a type of cannula.

A tympanic thermometer typically is required as a measurement of brain temperature. These are common items. Other thermometers may be used to measure a patient's temperature, but tympanic temperature is the easiest and most reliable method of gauging brain temperature, especially in the field. One non-limiting example of a tympanic thermometer is the Braun Thermoscan PRO 4000, Welch Allyn Medical Products, Skaneateles Falls, N.Y.

Although a patient may be flushed manually, using a large syringe loaded with cold-flush solution, the cold-flush solution preferably is delivered by any medically-acceptable pump, which facilitates control of flow rates over the typical 10 to 30 minutes of induction of emergency preservation. Suitable pumps are common and are known in the relevant medical arts. The pump preferably has a controllable flow rate and a gauge for determining flow rates. The flow rate of the pump may be fixed so long as the fixed flow rate is acceptable for induction of emergency preservation, for example, and without limitation, at about 1.6 L/min, and as a non-limiting example, ranging from about 1 L/min to about 2 L/min.

A kit for emergency preservation induction (EP-Kit) is a set of components necessary to induce emergency preservation as rapidly, easily and effectively as possible at the point of need, in the field, ambulance, emergency room, or hospital setting. Elements of the kit are packaged sterilely, as is necessary, appropriate or desired, and may be disposable. In one embodiment, the EP-Kit is an emergency use, sterile, disposable pack for induction of emergency preservation. The EP-Kit may include some or all of the following catheters and accessories, as well as standard use medical/surgical equipment and items, permitting rapid deployment and use in any emergency scenario leading to cardiopulmonary arrest and the need emergency preservation induction. Elements of the kit, when appropriate, are "configured to" work in conjunction with one another. By stating that an element or component of a kit is "configured to" do something, or similar terms and expressions, it is meant that a component of the kit is adapted to, or otherwise contains necessary components, adapters, etc., for that component to work in conjunction with another component of the kit. For example, and without limitation, a reservoir, pump, oxygenator and heat exchange may comprise suitable fluid adapters or interconnects so that each device is fluidly-coupled to the other so that cold-flush solution can pass from the reservoir and through the pump, oxygenator and heat exchange, in any useful or desired order, and into the arterial cannula/catheter for delivery to a patient. In such a case, the oxygenator is said to be configured to oxygenate the cold-flush solution and the heat exchange is configured to cool the cold-flush solution. Unless described otherwise, adapters, interconnects, power sources, and the like either are common items or are easily-configured items, the selection and/or design of which are considered to be variations well within the abilities of those of average skill in the relevant art.

It also will be appreciated that the number and variety of devices available in the medical arts to achieve a single goal, such as cannulation and sealing off of a blood vessel is immense. The goal of the present disclosure is to provide useful examples of the equipment and devices and instruments that may be used to implement the methods described herein, and is not meant to limit in any way the use of equivalent devices or instruments to implement the methods described herein. Non limiting examples of items that may be included in a kit are as follows.

An access or arterial cannulation set, for example, and without limitation, an arterial or aortic cannulation set, such as, without limitation, trocars, introducers and catheters that permit delivery of the cold-flush solution to the patient. The cannulation instruments are selected to facilitate systemic introduction of cold-flush solution into a patient or cadaver. In one embodiment, the cannulation instruments are selected to facilitate aortic cannulation via peripheral arterial vessels, direct thoracotomy, or transthoracic approaches, thereby facilitating the cold flush emergency preservation induction procedures. The cannulation instruments maybe color-coded to facilitate identification of specific components in the field. The kit may include one of more sets of trocars, introducers and catheters selected to facilitate cannulation by the femoral route, the thoracotomy route and the transthoracic route. The kit also may include catheter clips for safely and effectively securing catheters to the patient and stretcher during casualty/patient transport to prevent and/or minimize the chance/risk of catheter movement subsequent to placement and initiation of cold flush delivery. In one embodiment, the catheter includes a catheter sealing and/or occluding balloons and their pilot indicators to seal and secure catheters at vascular entry points as necessary to prevent leaks around the catheter and to isolate cold flush perfusions to brain and heart, spinal cord and abdominal organs, and/or global perfusion as determined appropriate during emergency preservation procedures.

The kit also may contain one or more of a venous decompression cannula, such as a needle, a catheter tube, a collection bag and securing clips for jugular, right atrial access, or other venous access, or like instruments, for collection of blood and fluid during cold flush perfusion in patients undergoing emergency preservation induction. Optionally, cold flush recirculation catheter needle(s), tubing loop(s) and securing clips for placing a peripheral, contralateral, venous-arterial or venous-venous connection to permit recirculation of cold flush through a system sterile cooling bag/chamber or heat exchanger to reduce and/or conserve the volume of required cold-flush solution. Cannulation catheter connectors may be provided for use in conversion to cardiopulmonary bypass and delayed resuscitation subsequent to emergency preservation induction. The cannulation catheter connectors may be color-coded and/or keyed.

One non-limiting example of useful cannulation instruments for the thoracotomy approach are a Medtronic 20-24 Fr cannula with blunt obturator and Carmeda-bonded for direct cannulation of the aorta and a Medtronic 32-40 Fr cannula, Carmeda-bonded for placement in the right atrium for decompression. The decompression cannula may or may not be needed depending on whether or not the atrial appendage is amputated. For percutaneous insertion, without limitation, a 21 Fr arterial cannula and a 27-29 venous cannula (both preferably Carmeda-bonded, available from Medtronic) may be used.

The kit preferably includes a container containing a cold-flush solution as described herein. The container may be insulated, or may be placed within an insulating compartment. The container is said to be "insulated" either if it is insulating by itself or if it is carried in the kit within an insulating compartment. The container may be any container that is suitable for carrying sterile medical fluids for parenteral administration, including, without limitation: infusion bags, infusion bottles, fluid reservoirs, and pressurized vessels. The kit also may contain a cold-flush solution infusion set, typically including a filter and a bubble trap for connection of the cannulation catheter to the cold-flush solution container. The infusion set also may contain tubing and tubing connectors for connection of the cold-flush solution container and cannulation instrument(s) to a cooling and/or pump unit.

The kit may include a suitable pump unit to facilitate constant delivery of the cold-flush solution to the patient or cadaver. The pump can be any medically-acceptable pump unit, for example, and without limitation, as are used in Heart-Lung Bypass (HLB) procedures.

The kit may include a cooling device for cooling, or maintain sufficiently low temperatures of the cold-flush solution as it is delivered to the patient or cadaver. Heat exchange and refrigeration units are known in the art. Non-limiting examples include those heat exchangers disclosed in U.S. Pat. Nos. 5,149,321 and 6,485,450, which are incorporated herein by reference in their entirety for their respective technical disclosures. Heart-Lung machines also contain heat exchangers, which may prove useful in lowering and maintaining the temperature of the cold-flush solution, though many such devices do not contain heat exchangers that are capable of lowering the temperature of the solution to 0° C. to 4° C. In such a case, a more potent heat exchange device, as are commercially available, may be used to chill the solution to the desired temperature.

Catheter priming solution, typically saline, also may be provided in the kit. In one embodiment the catheter priming saline is provided in filled, optionally color-coded, syringes. The catheters may be pre-filled with saline and sealed to ensure air elimination in catheter sets prior to cannulation and delivery of cold flush. Likewise, catheter inflation or sealing solution, typically saline, may be provided for inflation of catheter sealing and occluding balloons and their pilot indicators to seal and secure catheters at vascular entry points as necessary to prevent leaks around the catheter and to isolate cold flush perfusions to brain and heart, spinal cord and abdominal organs, and/or global (systemic) perfusion as determined appropriate during emergency preservation procedures. The catheter inflation or sealing solution may be provided in saline-filled syringes that are, optionally color-coded and limited volume.

The kit also may include a tympanic membrane temperature monitor, typically an infrared tympanic thermometer. The temperature monitor may include a lead and attachment/placement clip for monitoring tympanic membrane temperature as an indication of core brain temperature for providing temperature data to guide cold flush emergency preservation induction and profound hypothermia temperature maintenance.

The kit may include an indicia (a label, card, package insert, instructional sheet or other writing and/or illustration) including, for example and without limitation a printed checklist and text/diagrammatic instructions for use of EP-Kit materials for one or more of: patient evaluation, cannulation, cold flush delivery, emergency preservation induction, patient monitoring, emergency transport, cardiopulmonary bypass and/or delayed resuscitation phases.

The kit may further include instruments for vascular access, including, without limitation: scalpels, self-retaining retractors, hemostats, needle drivers and forceps. Other useful items may be included in the kit, including, without limitation: gloves, swab(s), sponge(s), sterile sheet(s), towel(s), tape to support the placement of cannulation catheters, and indicia describing and/or illustrating procedures for emergency preservation induction.

The kit may include, or be adapted to interface with sensors and a control unit or module—a controlling and monitoring device. The controlling and monitoring device may be a computerized device, for example and without limitation a PDA or modified PDA, and may include, without limitation a central processing unit (CPU) and hardware- or software-implemented processes for controlling and/or monitoring the status of the emergency preservation induction process and patient parameters, such as tympanic temperature, cold-flush solution temperature, solution flow rates. The computerized monitoring device also can be used to monitor position in the patient of the catheter. In embodiments of the kit that include or otherwise implement such a computerized monitoring/control device, the kit preferably would contain pre-configured and integrated temperature, pressure, flow and/or position sensors and leads for the catheter sets to provide data for manual and/or computer controlled emergency preservation cold flush delivery and emergency preservation induction. In such embodiments, the kit also may include sensor leads, which may be color-coded and/or keyed for plug-in a computerized emergency preservation system control unit/module for monitoring catheter position and for controlling and monitoring cold flush delivery, hypothermia induction, and hypothermia maintenance. U.S. Pat. Nos. 5,149,321 and 6,485,450 describe integrated fluid reservoirs, heat-exchangers, pumps and control (logic) devices useful in delivering cold-oxygenated fluids.

Certain, if not many of the items listed above may not be included in certain embodiments of the kit. Items not included in certain embodiments of the kit, for example, and without limitation: gloves, swabs and instruments for vascular access, may be provided separately. Other items, such as a pump, refrigeration/heat exchange device and a controlling and monitoring device, may be provided separately from the kit to be used in more than one emergency preservation induction. For example, if a peristaltic pump is provided separately, the kit may include disposable peristaltic tubing, and associated connectors, for use in the peristaltic pump. Likewise, for a refrigeration/heat exchange unit, a suitably-configured disposable insert module or cartridge having a fluid inlet and outlet, suitable fluid connectors and a heat-exchange surface interface, may be provided in the kit.

Preferably, the EP-Kit items, as is required, will be sterile-packed in multiple component plastic packs and boxed together for required, sequential and optimal use in emergency preservation procedures, with each pack clearly numbered and labeled for sequential use and quick, easy selection and deployment. The EP-Kit components are preferably specifically designed and configured to interface seamlessly with the novel and essential emergency preservation cold-flush solution bags and additives, catheter insertion and placement equipment, pumping/cooling equipment, and control system for sensor monitoring.

Figure 3:
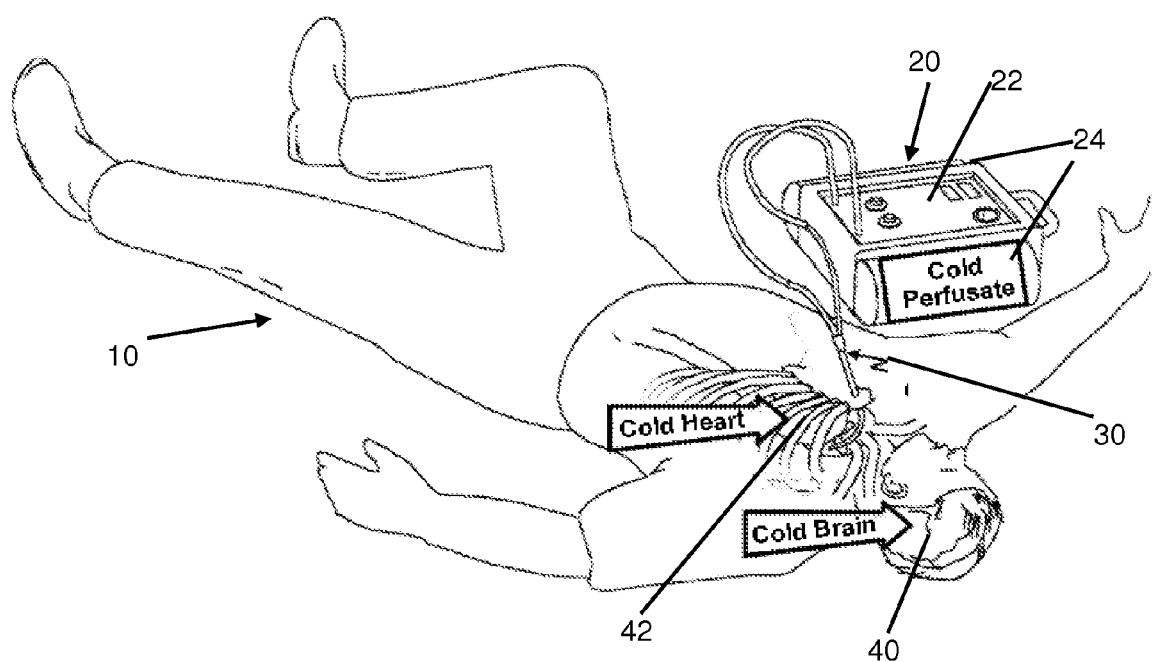
FIG. 3 illustrates a patient undergoing perfusion according to one embodiment of the present invention.

In use, the EP-Kit is used to perform life-saving procedures and techniques for heretofore unresuscitable/unrecoverable victims of trauma-induced severe hemorrhagic shock, exsanguination cardiopulmonary arrest and other terminal conditions (that now are potentially recoverable), who would otherwise die without these innovative medical emergency interventions/measures. Emergency preservation and delayed resuscitation methods, procedures and techniques are configured to integrate specific capabilities for profound to ultra-profound hypothermia induction in emergency room, in-hospital settings, and more importantly, at the point-of-injury by paramedics and medics, in a stepwise manner. FIG. 3 shows one embodiment of the present invention, in which a patient 10 is connected to a perfusion device 20 comprising a control module 22, cold perfusate reservoirs 24 and pumps internal to device 20 (not shown). Patient 10 is catheterized using a balloon catheter 30, with the overall goal of cooling brain 40 and heart 42 as well as other organs and systems.

Figure 4:
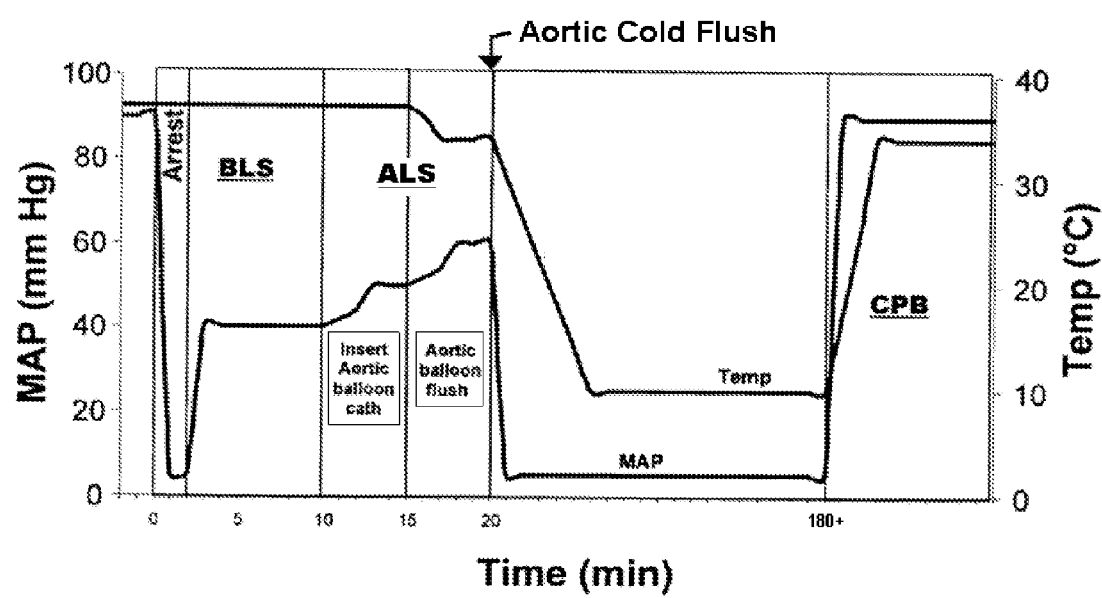
FIG. 4 is a graph illustrating one non-limiting embodiment of the present invention (Abbreviations: BLS=Basic Life Support; ALS=Advanced Life Support; MAP=Mean Arterial Pressure; and CPB=Cardiopulmonary Bypass).

As an example, for exsanguination, where uncontrolled bleeding leads to cardiopulmonary arrest, the victim may receive emergent aortic cannulation and jugular, right atrial or superior or inferior vena caval cannulation, as may be necessary for decompression. A rapid intra-aortic flush of >0° C. to about 4° C., preferably from about 1° C. to about 2° C., and most preferably about 2° C. normal saline fully saturated with dissolved oxygen and including 2.5% dextrose (cold energy), or equivalent for oxygen and energy delivery, is performed to achieve a target tympanic temperature of from about 4° C. to about 10° C., and preferably about 7° C. The cold flush should be completed (target temperature achieved) in less than about 30 minutes, preferably less that about 27 minutes and most typically from about 15 to about 20 minutes. Cold flush volume may require as much as 500-600 ml/kg. One non-limiting embodiment of the present invention, showing timing of the various procedures is provided in FIG. 4.

Figure 5:
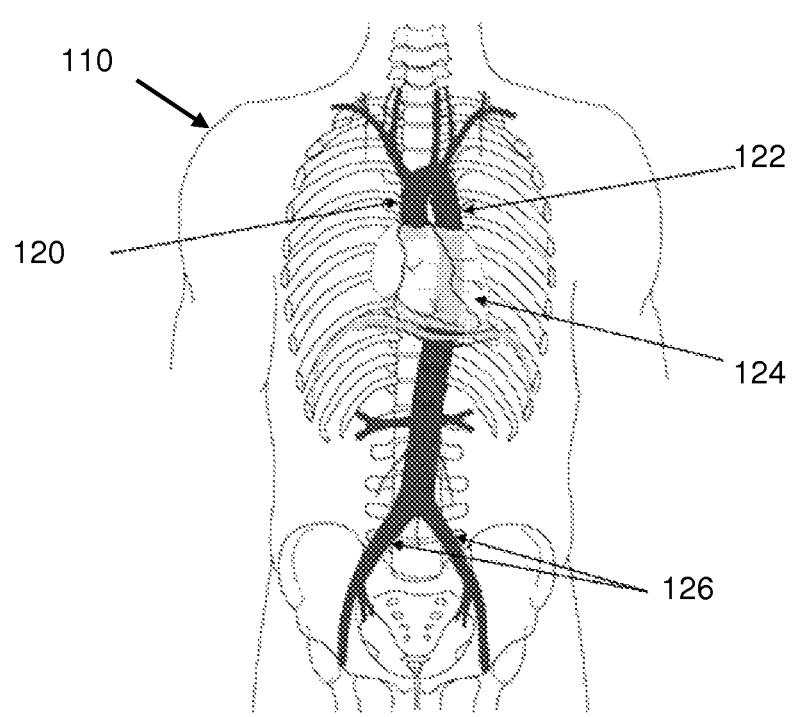
FIG. 5 is an illustration showing non-limiting examples of potential perfusion approaches in a patient.

Aortic cannulation for introducing the cold-flush solution into the patient is one example of how to flush a patient with cold-flush solution. The cold-flush solution may be introduced into the patient at sites other than the aorta, as are known in the medical arts. FIG. 5 shows four non-limiting potential perfusion approach routes in a patient 110, including, transthoracic ascending aorta approach 120, descending aorta approach via thoracotomy 122, left cardiac ventricle access via thoracotomy or left transthoracic approach 124 and right or left femoral artery approach 126. For example, in the experiments described below, a large bore, short cannula was placed into the femoral artery and flushed at a high rate into that site. The flush immediately transits into the descending aorta and travels both retrograde and antegrade to perfuse the entire organism. In the trauma bay, with the aorta visualized, one might prefer to directly catheterize the aorta. In the field, it might prove easier to catheterize the femoral artery.

Drainage of the flush solution typically occurs spontaneously from the jugular, atrial or vena caval cannula(e). The cold energy solution may be delivered using common or specially-designed apparatus and catheters. The cold energy solution may also include oxygen carriers such as an artificial hemoglobin or blood substitutes of all types and/or other energy substrates as described above. Resuscitation is performed after surgery using cardiopulmonary bypass. It is important to maintain the victim under mild hypothermia (typically, and without limitation, the point at which a spontaneous heartbeat can be obtained, about 34° C.), preferably with full intensive care unit capabilities, for approximately 48-72 hours with very slow re-warming once a temperature of about, for example and without limitation, 34° C. is reached. This entire procedure would be identical in the setting of normovolemic cardiopulmonary arrest with the exception that surgery would not be required to repair tissue trauma, but definitive therapy could include interventions such as initiation of cardiopulmonary bypass, implementation of an artificial heart, or administration of anti-toxin, anti-venom, or other appropriate antidote or therapy.

Emergency preservation and resuscitation, as described herein can produce intact survival with normal neurological outcome even when prolonged hemorrhagic shock precedes exsanguination cardiopulmonary arrest. These observations support the use of emergency preservation and resuscitation after exsanguination cardiopulmonary arrest resulting from either rapid exsanguination or slower bleeding coupled with prolonged hemorrhagic shock following traumatic injury, thus broadening the potential target for use of emergency preservation and resuscitation in military and civilian trauma.

Prolonged preservation and resuscitation beyond 3 hours (3+ hours) designed to provide extended preservation times to facilitate transport and emergency room interventions may be achieved with energy substrates, including oxygen and glucose, that may be added to the cold-flush solution to achieve 3 or more hours of preservation prior to delayed resuscitation with intact neurological outcomes. Any alternatives or enhancements for oxygen and glucose delivery may also be included in the cold flush, or cold energy flush, including oxygen carrying hemoglobin blood substitutes, antioxidants, perfluorocarbons, glucose analogs and/or other energy substrates and other drugs/additives than enhance the brain utilization of oxygen and glucose.

During the delayed resuscitation phase, with the victim on cardiopulmonary bypass, re-warming may rapidly proceed to mild-to-moderate hypothermic levels to obtain a stable circulation off of cardiopulmonary bypass, which typically is at from about 33° C. to about 36° C. Although a heartbeat will appear at from about 16° C. to about 18° C., stable, optimal cardiovascular hemodynamics are not found until from about 33° C. to about 36° C., permitting eventual removal from bypass. At that point, further re-warming to normothermia should be accomplished very slowly over the next 24-72 hours to improve outcome recovery and survivals. This is an important step in achieving successful emergency preservation and delayed resuscitation to full recovery, particularly following prolonged preservation of 3 hours and beyond.

In certain embodiments, specific procedures that preferably are integrated for successful emergency preservation and delayed resuscitation include the following components:

Patient/Victim Assessment for Emergency Preservation Induction.

The assessment of a patient/victim for appropriate, safe and efficacious induction of emergency preservation will be performed by the physician, civilian paramedic or military medic. Assessment may be performed using a strict set of clinical criteria that may be determined and analyzed via a printed checklist and text/diagrammatic instructions (indicia), optionally provided in a EP-Kit. This specifically assists the physician, paramedic and military medic in decision support for induction of emergency preservation.

Vascular Access Approaches.

Induction of emergency preservation requires rapid vascular access via several, optional approaches for cannulation, cold flush, and catheter (or cannula, as the case may be) placement, as described above. As described above, approaches to the thoracic aorta include: thoracotomy and cannulation; transthoracic placement and advancement of a catheter in the aorta; and placement and advancement of a catheter via peripheral vasculature. As described above, access to the thoracic aorta is effective but not essential. A large bore femoral artery catheter is equally effective and could ultimately be the preferred site. That approach would deliver the flush initially to the distal abdominal aorta.

EP-Kit Catheter/Cannula Features for Targeted Organ and Global Cold Flush.

The concepts for cold flush catheters/cannulae cover the design aspects that permit the catheter/cannula to be easily placed in the thoracic/descending aorta, femoral artery or other entry sites, as described herein, as well as sealing at the insertion point to prevent cold flush leakage. For example and without limitation, catheters would include aortic or femoral artery occluding balloons that when inflated, at the initial induction of emergency preservation, direct cold-flush solutions preferentially to the brain and heart for rapid cooling and economy of cold flush volumes, thereby protecting the brain, heart and spinal cord as quickly as possible with profound to ultra-profound hypothermic temperatures. The appropriate deflation of the occluding balloon then permits flow throughout the rest of the body to provide global cooling and preservation, as is necessary for prolonged preservation periods beyond 30 minutes. Although it is extremely important to flush the brain, heart and spinal cord, whole body flushing is preferred for extended preservation (greater than 90 minutes) over localized flushing of the brain, heart and spinal cord. Inflation of the aortic or femoral balloon may be maintained to decrease blood loss from more distal arterial injuries.

Catheter Placement Techniques for Rapid Access to the Aorta.

Devices may be used that facilitate insertion, guidance and placement of the specific catheters into the thoracic/descending aorta, femoral artery or other entry site for emergency preservation induction procedures. These devices may be designed for use specifically in the EP-Kit for emergency preservation induction.

Integrated System Controls and Patient/Victim Monitoring.

Following placement of a catheter/cannula into the desired entry site, such as the thoracic/descending aorta or femoral artery, cold flush must be initiated. This may be initiated according to recommended choices for cold flush and substrate solutions, flow rates, cold flush volumes, core temperature targets and maintenance as measured by tympanic membrane temperatures, catheter sensors, cold flush recirculation flow rates and venous decompression needs. These parameter monitoring needs, analyses and recommended and/or automated adjustments may be performed by a computerized emergency preservation induction control system connected to color-coded and keyed sensor leads from the EP-Kit.

Cold Flush Perfusion and Recirculation.

Ideally cold flush typically should be administered within 5 minutes of cardiopulmonary arrest. The cold flush is delivered to the brain and heart initially, as rapidly as possible, to bring the tympanic membrane temperature, as an indication of core/brain temperature, to within deep or profound (6° C.-20° C.) hypothermia levels. Cold-flush solution temperatures (typically 1° C. to 2° C.) and volumes (up to 30-40 liters), catheter/cannula capacities, and pumps preferably would sustain 1.5 to 2 liter flow rates per minute, as may be determined necessary, to bring tympanic temperature to profound hypothermia levels, for example, from about 7° C. to about 8° C. The required cold flush volumes may be significantly reduced (5-8 times) and efficiency of rapid cooling enhanced by establishing a venous-arterial recirculation loop through a cooling heat exchanger, and optionally an oxygenator, to recycle cold flush while maintaining profound hypothermic temperatures. Recirculation may not be possible if the injuries include major vascular disruptions. The cold-flush solution and recirculation loop typically would be delivered and maintained, for example and without limitation, via catheter, infusion sets, recirculation loops and connections provided with the EP-Kit.

Cooling and Pump Device.

Cooling devices (heat exchangers) are able to maintain cold energy flush solution at 1° C. to 2° C., ready for induction of emergency preservation. The cooling device heat exchanger can also maintain target temperature during emergency preservation by cooling flush solutions that then recirculate through a venous-arterial loop to reduce cold flush volume needs while maintaining target temperatures for emergency preservation. The kit also may include a pump for rapid infusion of the cold flush and flush recirculation, which may be integrated with the cooling device.

Power Supplies for Refrigeration, Pump, Sensors and Control Units.

In certain non-limiting embodiments of the present invention, described Emergency Preservation and Resuscitation equipment and components include, without limitation, refrigeration units for producing the cold flush solution, pump units for delivering the cold flush solution, sensors incorporated into components for determining brain temperature, cold flush delivery rate, pressure and temperature, as well as the operation of any control units. These devices require power sources, such as, without limitation, standard hospital electrical supply, generally but not limited 110/115 volt AC power, available DC power, such as, without limitation, standard medical and military lithium, Ni—Cd, gel cells, fuel cell batteries or other DC batteries, and power sources available on medical ambulance and emergency vehicles. The critical pump operation for delivery of cold flush solutions may be configured for hand-crank delivery of cold flush solutions as may be necessary in the field and/or remote locations.

Safety Features for Equipment.

In certain non-limiting embodiments of the kit, equipment is fitted with alarm and maximum operation safety features to ensure that cold flush solutions are maintained at required temperatures before delivery, that maximum pump delivery rates and pressures for a specific emergency scenario are not exceeded, and that other sensors and components are operating as required for individual components and integrated systems.

Transition to Cardiopulmonary Bypass.

The catheters/cannulae inserted into the vascular entry site via any access approach may be configured to be used for arterial side connection to a cardiopulmonary bypass machine once the victim is transported to an emergency facility and is ready for delayed resuscitation.

Re-warming to Mild-to-Moderate Hypothermia and Normothermia.

During the delayed resuscitation phase, with the victim on cardiopulmonary bypass, re-warming may proceed to moderate (26° C. to 32° C.) to mild (33° C. to 36° C.) hypothermic levels to obtain stable, optimal cardiovascular hemodynamics. At that point, further re-warming to normothermia should be accomplished very slowly over the next 24-72 hours to improve outcome recovery and survival. The veno-arterial or veno-venous catheters/cannulae and recirculation loop for maintaining target hypothermia temperatures provided in the EP-Kit may also be used to maintain the patient in mild-to-moderate hypothermia post-resuscitation.

A non-limiting summary outline of one example of emergency preservation and resuscitation procedures and techniques that utilize components of an EP-Kit is as follows:

(1) Train paramedics, medics, physicians, trauma surgeons and/or other medical personnel for emergency preservation procedures and devices;
(2) Assess victim for emergency preservation induction using assessment and instruction card;
(3) Assess and select vascular access approach;
(4) Prime and place access catheter/cannula;
(5) Secure catheter/cannula placement including inflation of self-sealing balloons;
(6) Setup and prime cold energy flush supply and pump system;
(7) Connect access catheter to cold energy flush;
(8) Establish recirculation loop for cold flush or venous decompression option;
(9) Check system, line and connections;
(10) Optionally inflate catheter occluding balloon;
(11) Initiate rapid cold energy flush perfusion and recirculation;
(12) Monitor profound hypothermia target brain temperature;
(13) Optionally deflate occluding balloon following heart and brain cooling and start global cooling;
(14) Maintain emergency preservation and tympanic target temperature;
(15) Modulate recirculation as may be necessary to maintain target temperature;
(16) Transport patient to medical facility;
(17) Perform critical medical/surgical interventions;
(18) Place patient on cardiopulmonary bypass for delayed resuscitation;
(19) Continue medical/surgical interventions as may be necessary;
(20) Re-warm patient to mild-to-moderate hypothermia to obtain initially a heartbeat and then stable hemodynamics for potential removal from cardiopulmonary bypass;
(21) Perform plasma exchange or equivalence as deemed necessary for the situation;
(22) Remove patient from cardiopulmonary bypass;
(23) Connect extracorporeal mild-to-moderate cooling device for continuing hypothermia;
(24) Maintain the patient in mild-to-moderate hypothermia for 1-2 days; and
(25) Re-warm patient to normothermia and remove extracorporeal cooling device.

Indicia provided with the kit may contain instructions and/or diagrams on how to perform some, many or all of the steps listed above, for example, and without limitation, steps 2-15 or steps 2-9, 11, 12, 14 and 15.

Example 1

Resuscitation of Dogs after Three Hours Emergency Preservation

The experimental protocol was approved by the Institutional Animal Care and Use Committee of the University of Pittsburgh and the Department of Defense and followed the national guidelines for treatment of animals.

Experimental Design

Model: The model included 3 phases: 1) Hemorrhage and cardiac arrest (CA) phase (5 min of hemorrhage followed by 2 min of CA; 2) emergency preservation (EP) phase (3 h), and 3) delayed resuscitation phase, including cardiopulmonary bypass (CPB) (2 h) and full intensive care unit (ICU) Care (72 h).

Groups: At the end of Hemorrhage and CA phase, dogs were randomized into following 4 groups as the following:

| | 2.5% glucose/saline flush | $O_2/N_2$ insufflation via CPB machine |
|---|---|---|
| Group $G+O_2+$ (n = 6) | 2.5% glucose in NS | $O_2$ |
| Group $G-O_2+$ (n = 6) | NS | $O_2$ |
| Group $G+O_2-$ (n = 6) | 2.5% glucose in NS | $N_2$ |
| Group $G-O_2-$ (n = 6) | NS | $N_2$ |

Anesthesia and Preparation

Custom-bred, male hunting dogs, weighing 19.5-24.0 kg, were housed for at least 3 days before the experiment. A total of 24 dogs were use and no dog had ever been excluded for any reason. Dogs were fasted with free access to water for 12 h. Ketamine 10 mg/kg and atropine 0.4 mg was administered intramuscularly. Following anesthesia induction with 4% halothane via face mask, endotracheal intubation (ID 8-9 mm) was performed. Continuous anesthesia was provided with halothane ~1%, titrated during preparation ($O_2:N_2O$: 50%: 50%). Controlled ventilation was initiated with tidal volume 12-15 ml/kg, positive end expiratory pressure (PEEP) 2 cm $H_2O$, and frequency 20-25/min, titrated to maintain $PaCO_2$ 35-45 torr. Electrocardiogram (EKG) lead II was continually monitored. A cannula (18 G) was inserted into a peripheral vein and fluid infusion (D5W/0.45 NaCl at 4 ml/kg/h) was started. A Foley catheter was placed into the urinary bladder. Temperature probes were inserted for measuring rectal, esophageal, and both tympanic membrane temperatures (Tty). Sterile cutdowns were made in both groins and the right side of the neck. A PE 90 catheter was inserted into the left femoral artery for blood pressure monitoring and blood samples. A pulmonary artery catheter (7.5 F) was inserted via the left femoral vein into the pulmonary artery to monitor pressure, cardiac output, and core temperature (Tpa). A CPB arterial cannula (7 or 9 G) was inserted into the right femoral artery. A multiple-hole cannula (19 F) was inserted 25 cm into the right external jugular vein. The CPB system consisted of a hollow-fiber membrane oxygenator (Medtronic, Grand Rapids, Mich.) and centrifugal pump (Biomedicus, Eden Prairie, Minn.). For induction of emergency preservation, the CPB system was primed with flush solution; for delayed resuscitation after emergency preservation, the system was primed with shed blood (30 ml/kg) and Plasma-Lyte A (Baxter, Deerfield, Ill.).

Baseline measurements (hemodynamics, arterial and venous blood gases, body temperature) were collected when and the animal was stable, usually 15-30 min after surgical preparation.

Hemorrhage and CA Phase

After two baseline measurements, heating, intravenous fluids, and halothane were discontinued, and the dogs were weaned to spontaneous breathing of air via a T-tube. When the canthal reflex returned, hemorrhage was initiated via the venous cannulae (simulating traumatic laceration) and the blood was collected in bags with sodium citrate anticoagulant for later reinfusion. Hemorrhage was controlled to mean arterial pressure (MAP) 20 mm Hg at 4 min. At 5 min, ventricular fibrillation was induced to ensure zero blood flow with transthoracic AC at 95 V. Ventricular fibrillation (VF) was confirmed with EKG.

Emergency Preservation Phase

Two minutes after the onset of CA, flush solution (80 ml/kg) at 2° C. was flushed into the aorta at a rate of 80 ml/kg/min with a CPB machine. The close-chest CPB from the left external jugular vein to the left femoral artery was then initiated for induction of hypothermia until Tty reached 8° C. Either 100% $O_2$ or $N_2$ was supplied to the oxygenator throughout the whole flush and CPB. The gas rate to the CPB oxygenator was adjusted to ensure a normal $pCO_2$ 35-45 mmHg per blood gas analysis results. The whole body was covered with ice from the onset of flush to the end of 3 h CA.

Delayed Resuscitation Phase.

CPB Three hours after occurrence of CA, reperfusion was started with CPB that was primed with shed blood with heparin 1000 units. Just before the start of CPB, sodium bicarbonate (1 mEq/kg) and epinephrine 0.01 mg/kg were injected into the circuit. The temperature of the water bath of the CPB heat exchanger was set to 5° C. above Tpa until Tpa reached 34° C. CPB was started with a flow of 50 $mL \cdot kg^{-1} \cdot min^{-1}$ when Tpa<20° C., increased to 75 $mL \cdot kg^{-1} \cdot min^{-1}$ when Tpa 21° C.-30° C., and increased to 100 $mL \cdot kg^{-1} \cdot min^{-1}$ when Tpa>30° C. Reinfusion of all shed blood was titrated to achieve a central venous pressure of 10-15 mm Hg. Repetitive doses of epinephrine (0.01 mg/kg) were given intra-arterially to increase MAP to 60 mm Hg when Tpa<20° C., to 80 mm Hg when Tpa 21-30° C., and to 100 mm Hg when Tty>30° C. When Tpa reached 32° C., defibrillation was attempted with external DC countershocks of 150 J, increased by 50 J for repeated shocks. Oxygen flow through the oxygenator was adjusted to keep $Paco_2$ at 30-35 mm Hg and $Pao_2 \geq 100$ mm Hg. During CPB of 2 hrs, controlled ventilation was with 100% oxygen at a rate of eight to ten cycles per minute. The intravenous fluids were restarted at 4 mL/kg/hr. A base deficit of >6.0 mEq/L was corrected with sodium bicarbonate. MAP was controlled at 90-150 mm Hg. The CPB flow rate for assisted circulation was reduced to 75 and 50 $mL \cdot kg^{-1} \cdot min^{-1}$ and stopped at 120 mins. During CPB, activated clotting times were maintained at >300 secs with additional heparin.

ICU The details of life support, including mechanical ventilation, hemodynamic monitoring and support, and correction of acid-base or electrolyte abnormalities, were published previously (Behringer W, S afar P, Wu X, Kentner R, Radovsky A, Kochanek P M, Dixon C E, Tisherman S A., "Survival without brain damage after clinical death of 60-120 mins in dogs using suspended animation by profound hypothermia," *Crit Care Med* 31:1523-31, 2003). ICU care, including mechanical ventilation, was provided for 48 h. The body temperature was kept at 34° C. until 36 h of delayed resuscitation, followed by slow re-warming (0.3° C./h). At 48 h, anesthetics were discontinued and muscle relaxant was reversed. Dogs were then weaned from mechanical ventilation. Following extubation, they were transferred to the step-down unit where continuous i.v. fluid and vital sign monitoring were provided until 72 h.

Outcome Evaluation

Functional outcomes were evaluated every 6 h in the step-down unit according to overall performance categories (OPC) (OPC 1=normal or slight disability; 2=moderate disability; 3=severe disability; 4=coma; and 5=death) and neurologic deficit scores (NDS) (NDS 0-10%=normal; 100%=brain death), which includes level of consciousness, breathing pattern, cranial nerve function, sensory and motor function, and behavior. Blood samples were obtained at baseline and every 24 h for cardiac (troponin I, creatine phosphokinase MB fraction) and liver enzymes (transaminases and bilirubin). At 72 h, a final functional assessment was performed and animals were then re-anesthetized with ketamine and halothane. Perfusion-fixation was performed with cephalad infusion of 10% neutral buffered formalin via the thoracic aorta. A gross necropsy was subsequently performed. The entire brain was removed approximately 2 h after perfusion fixation and retained in 10% neutral buffered formalin until the time of dissection.

Neuropathology

Whole perfusion-fixed brains were divided into multiple coronal slices. Six coronal brain slices plus three transverse sections of the medulla oblongata and upper cervical cord were selected for microscopic evaluation. These represented entire brain slices taken at the following levels: 1) Level of the optic chiasm; 2) Level of the anterior thalamus; 3) Level of the posterior thalamus; 4) Level of the midbrain; 5) Posterior portions of the occipital lobes; 6) Middle of the cerebellum and underlying brainstem; 7) medulla oblongata and upper cervical cord. Each brain slice was divided into between two and four pieces so that the sections would fit onto standard 1×3 inch microscope slides (excepting for the sections through the medulla oblongata and cervical cord). These brain slices were processed for paraffin embedding, resulting in 20 tissue blocks from each brain. The paraffin blocks were sectioned at 5 micrometers and the resulting sections stained with hematoxylin and eosin (H&E) and with Fluoro-Jade B. The examining neuropathologist was blinded as to the treatment groups. Each neuroanatomic region with evidence of damage on microscopic examination received a subjective pathologic grade ranging from 1+(minimal) to 5+(severe). Each affected region on each side of the brain (right and left) received separate scores for the degrees of neuropathologic damage detected in H&E-stained and Fluoro-Jade B-stained sections. The Histological Damage Scores (HDS) were determined by adding up all of these individual scores (i.e. for each region with each stain).

Statistical Analysis

Data are presented as mean±standard deviation unless otherwise stated. Repeated measures analyses of variance were performed followed by Bonferroni post-hoc tests to identify differences in hemodynamic parameters and temperature between groups. NDS and HDS scores were analyzed using Mann-Whitney U Test, and Fisher's exact test was used to assess differences in OPC proportions (i.e., good outcome [OPC 1] versus bad outcome [OPC 2-5]) between groups. A p-value<0.05 was considered statistically significant.

Results

Figure 2:
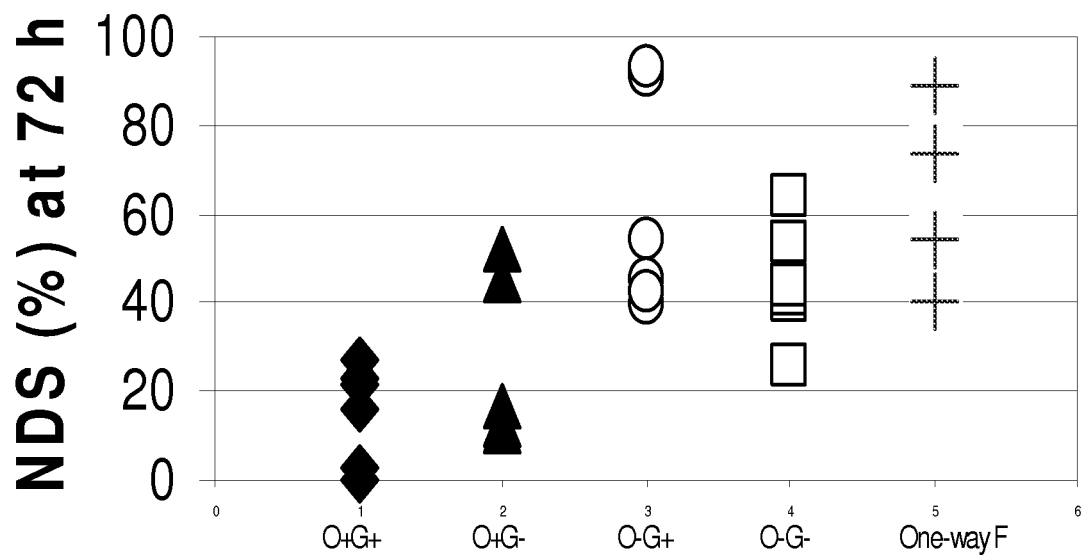
FIG. 2 is a graph showing the final neurological deficit scores (NDS) in dogs at 72 h after emergency preservation for 3 h post-cardiac arrest.

The total flush time to reach Tty 8° C. was similar between groups. Two $G^+$ groups had significantly lower sodium levels (p<0.05), numerically lower perfusion pressures (NS), and hematocrit (NS) at the end of flush (Table 1). Two $O^+$ groups had significantly lower potassium than the other two groups (p<0.01) (Table 1). The lactate levels were significantly higher in the two $O^-$ groups during early delayed resuscitation phase (p<0.05) (FIG. 1). At 72 h, all animals in the $G^+O^+$ group regained consciousness with a significantly better NDS (FIG. 2) and better OPC (Table 2) (both p<0.05), compared to the $O^-$ groups. In the Group $G^-O^+$, only 4 dogs regained consciousness (NS v. other groups). All but 1 dog in the $O^-$ groups remained comatose. Neuropathological results are pending.

TABLE 1

Physiological parameters at the end of emergency preservation induction

| Groups | Group G+O+ | Group G−O+ | Group G+O− | Group G−O− |
|---|---|---|---|---|
| Total Flush Time (min) | 26.2 ± 1.5 | 26.0 ± 2.3 | 24.9 ± 2.2 | 27.1 ± 2.3 |
| Glucose(mg/dl) | 975 ± 186 | 175 ± 60 | 957 ± 295 | 288 ± 15 |
| $PO_2$ (mmHg) | 432 ≥ 800 | 410 ≥ 800 | 23.5 ± 7.8 | 18.6 ± 8.1 |
| pHa | 7.2 ± 0.1 | 7.1 ± 0.0 | 7.1 ± 0.0 | 7.1 ± 0.1 |
| $PCO_2$ (mmHg) | 34.4 ± 3.8 | 41.6 ± 3.4 | 35.3 ± 4.4 | 39.9 ± 4.1 |
| BE (mmol/L) | −13.8 ± 3.0 | −13.1 ± 3.5 | −15.5 ± 1.0 | −15.2 ± 1.9 |
| Lactate (mmol/L) | 6.4 ± 1.0 | 6.1 ± 1.7 | 7.6 ± 1.0 | 8.8 ± 0.8 |
| Hematocrit (%) | 11.3 ± 2.8 | 15.5 ± 2.8 | 9.5 ± 4.3 | 14.7 ± 3.5 |
| Sodium (mmol/L) | 132.9 ± 7.1 | 147.3 ± 2.3 | 136.6 ± 0.8 | 145.9 ± 1.4 |
| Potassium (mmol/L) | 3.5 ± 0.3 | 3.1 ± 0.2 | 4.8 ± 0.6 | 5.0 ± 0.6 |

TABLE 2

Final OPC at 72 h after emergency preservation for 3 h cardiac arrest

| | Group G+O+ | Group G−O+ | Group G+O− | Group G−O− |
|---|---|---|---|---|
| 5 Dead | | | | |
| 4 Coma | | * | * * * | * * |
| 3 Severe Disability | | * | * * * | * * * |
| 2 Moderate Disability | * * * * | * * | | * |
| 1 Normal | * * | * * | | |

* = one dog

CONCLUSIONS

A combination of oxygen (saline saturated with $O_2$ via oxygenator) and 2.5% glucose—added to the saline flush solution—is critical for successful resuscitation of 3 h exsanguination CA with hypothermic emergency preservation protocol. Improved energy metabolism with oxygen, among other mechanisms, may be responsible for the remarkable beneficial effects observed.

Whereas particular embodiments of the invention have been described herein for the purpose of illustrating the invention and not for the purpose of limiting the same, it will be appreciated by those of ordinary skill in the art that numerous variations of the details, materials and arrangement of parts may be made within the principle and scope of the invention without departing from the invention as described in the appended claims.

We claim:

1. A method of inducing preservation in a patient suffering from cardiopulmonary arrest, comprising cooling the patient within about 8 minutes of cardiopulmonary arrest or cessation of cardiopulmonary resuscitation by flushing the patient's vasculature, including at least the patient's heart and brain, with an oxygenated, aqueous cold-flush solution comprising an energy source, wherein the cold-flush solution is introduced into the patient at from about 1° C. to about 4° C. and the patient is cooled to a tympanic temperature of less than 10° C. in a time period of less than 27 minutes.

2. The method of claim 1, wherein the patient is cooled to a tympanic temperature of about 7° C.

3. The method of claim 1, wherein the patient is cooled to a tympanic temperature of less than 10° C. in a time period of less than 20 minutes.

4. The method of claim 3, wherein the patient is cooled to a tympanic temperature of about −7° C. in a time period of less than 20 minutes.

5. The method of claim 1, wherein the patient is warmed within about three hours of initiation of preservation by introducing blood into the patient's vasculature and warming the patient to a state of mild hypothermia at from about 33° C. to about 36° C.

6. The method of claim 5, comprising raising the patient's temperature from mild hypothermia to about 37° C. over a time period of from about 24 to about 72 hours.

7. The method of claim 5, comprising raising the patient's temperature from mild hypothermia to about 37° C. over a time period of from about 48 to about 72 hours.

8. The method of claim 1, wherein the cold-flush solution is introduced into the patient through the patient's aorta.

9. The method of claim 1, wherein the cardiopulmonary arrest follows exsanguination.

10. The method of claim 1, wherein the cardiopulmonary arrest follows from about 2 hours to about 6 hours of hemorrhagic shock.

11. The method of claim 1, wherein the cardiopulmonary arrest is substantially normovolemic.

12. The method of claim 1, wherein the cardiopulmonary arrest follows a poisoning event.

13. The method of claim 1, wherein the cold-flush solution further comprises one or more nitroxide antioxidants.

14. The method of claim 13, wherein the one or more nitroxide antioxidants are selected from the group consisting of TEMPO and TEMPOL.

15. The method of claim 1, wherein the cold-flush solution further comprises TEMPOL.

16. The method of claim 1, wherein the cold-flush solution is introduced into the left ventricle of the patient.

17. The method of claim 1, wherein the cold-flush solution is normal saline.

18. The method of claim 1, wherein the cold-flush solution comprises an oxygen carrier.

19. The method of claim 1, wherein the oxygen carrier is one or both of polynitroxylated albumin and polynitroxylated hemoglobin.

20. The method of claim 1, wherein the energy source is glucose.

21. The method of claim 20, wherein the energy source is from about 0.1% w/v to about 5% w/v glucose.

22. The method of claim 20, wherein the energy source is about 2.5% glucose.

23. The method of claim 1, wherein the cold-flush solution is a saline solution.

24. The method of claim 23, wherein the saline solution is from about 0.85% w/v to about 1.5% w/v saline.

25. The method of claim 23, wherein the cold-flush solution is isotonic.

26. The method of claim 23, wherein the cold-flush solution is mildly hypertonic.

27. The method of claim 1, wherein the cold-flush solution is isotonic.

28. The method of claim 1, wherein the cold-flush solution is mildly hypertonic.

29. The method of claim 1, wherein the cold-flush solution comprises a neuroprotective agent.

30. The method of claim 29, wherein the neuroprotective agent is one or more agents selected from the group consisting of an anesthetic, an anticonvulsant, an anti-apoptotic agent and an anti-inflammatory agent.

31. The method of claim 29, wherein the neuroprotective agent is one or more agents selected from the group consisting of a barbiturate, thiopental, pentobarbital, ketamine, an opioid, phenytoin, valproate, a caspase inhibitor, a kinase inhibitor, a mitogen-activated protein kinase inhibitor, a protease inhibitor, a calpain antagonist, a cyclosporin, FK 506, methyl prednisolone, a cyclooxygenase-2 antagonist, an antagonists of a pro-inflammatory cytokine(s), TNF-alpha, IL-1 and IL-10.

32. The method of claim 1, wherein the cold-flush solution comprises one or both of ATP and an inorganic phosphate.

33. A method of preserving organs of a cadaver, comprising, cooling the cadaver by flushing the cadaver's blood vessels, including at least the cadaver's heart and brain, with an oxygenated cold-flush solution comprising an energy source, wherein the cooling solution is about 1° C. to about 4° C. and the cadaver is cooled to a tympanic temperature of less than 10° C. in a time period of less than 27 minutes.

34. The method of claim 33, wherein the energy source is glucose.

35. The method of claim 34, wherein the energy source is from about 0.1% w/v to about 5% w/v glucose.

36. The method of claim 33, wherein the energy source is about 2.5% glucose.

37. The method of claim 33, wherein the cold-flush solution is a saline solution.

38. The method of claim 37, wherein the saline solution is from about 0.85% w/v to about 1.5% w/v saline.

39. The method of claim 37, wherein the cold-flush solution is isotonic.

40. The method of claim 37, wherein the cold-flush solution is mildly hypertonic.

41. The method of claim 33, wherein the cold-flush solution is isotonic.

42. The method of claim 33, wherein the cold-flush solution is mildly hypertonic.

43. The method of claim 33, wherein the cold-flush solution comprises a neuroprotective agent.

44. The method of claim 43, wherein the neuroprotective agent is one or more agents selected from the group consisting of an anesthetic, an anticonvulsant, an anti-apoptotic agent and an anti-inflammatory agent.

45. The method of claim 43, wherein the neuroprotective agent is one or more agents selected from the group consisting of a barbiturate, thiopental, pentobarbital, ketamine, an opioid, phenytoin, valproate, a caspase inhibitor, a kinase inhibitor, a mitogen-activated protein kinase inhibitor, a protease inhibitor, a calpain antagonist, a cyclosporin, FK 506, methyl prednisolone, a cyclooxygenase-2 antagonist, an antagonists of a pro-inflammatory cytokine(s), TNF-alpha, IL-1 and IL-10.

46. The method of claim 33, further comprising re-introducing blood into the cadaver, warming the cadaver and harvesting an organ of the cadaver.

47. The method of claim 33, further comprising harvesting an organ of the cadaver.

48. The method of claim 33, wherein the cold-flush solution comprises one or both of ATP and an inorganic phosphate.

* * * * *

UNITED STATES PATENT AND TRADEMARK OFFICE
CERTIFICATE OF CORRECTION

PATENT NO. : 8,628,512 B2  
APPLICATION NO. : 12/900917  
DATED : January 14, 2014  
INVENTOR(S) : Patrick M. Kochanek et al.

It is certified that error appears in the above-identified patent and that said Letters Patent is hereby corrected as shown below:

On Title Page 2, Column 2, Item (56) OTHER PUBLICATIONS, Line 2, delete "neorologic" and insert -- neurologic --

On Title Page 2, Column 2, Item (56) OTHER PUBLICATIONS, Line 3, delete "exsandguination" and insert -- exsanguination --

In the Claims

Column 23, Line 66, Claim 4, delete "-7°C." and insert -- 7°C. --

Signed and Sealed this  
Twenty-ninth Day of April, 2014

Michelle K. Lee  
*Deputy Director of the United States Patent and Trademark Office*